US010881418B2

(12) United States Patent
Ecker et al.

(10) Patent No.: US 10,881,418 B2
(45) Date of Patent: Jan. 5, 2021

(54) ELECTRICALLY CONTROLLABLE SURGICAL TOOLS

(71) Applicant: Maine Medical Center, Portland, ME (US)

(72) Inventors: Robert D. Ecker, Cape Elizabeth, ME (US); Mohsen Shahinpoor, Bangor, ME (US)

(73) Assignee: Maine Medical Center, Portland, ME (US)

( * ) Notice: Subject to any disclaimer, the term of this patent is extended or adjusted under 35 U.S.C. 154(b) by 366 days.

(21) Appl. No.: 15/787,734

(22) Filed: Oct. 19, 2017

(65) Prior Publication Data

US 2018/0110536 A1 Apr. 26, 2018

Related U.S. Application Data

(60) Provisional application No. 62/410,830, filed on Oct. 20, 2016.

(51) Int. Cl.
| | | |
|---|---|---|
| *A61B 17/22* | (2006.01) | |
| *A61B 17/50* | (2006.01) | |
| *A61B 34/30* | (2016.01) | |
| *A61B 5/02* | (2006.01) | |
| *A61B 5/0215* | (2006.01) | |
| *A61B 5/026* | (2006.01) | |
| *A61B 17/00* | (2006.01) | |
| *A61B 17/12* | (2006.01) | |

(52) U.S. Cl.
CPC ........ *A61B 17/22031* (2013.01); *A61B 5/026* (2013.01); *A61B 5/02007* (2013.01); *A61B 5/0215* (2013.01); *A61B 17/22012* (2013.01); *A61B 17/22022* (2013.01); *A61B 17/50* (2013.01); *A61B 34/30* (2016.02); *A61B 2017/00017* (2013.01); *A61B 2017/00022* (2013.01); *A61B 2017/00292* (2013.01); *A61B 2017/12054* (2013.01); *A61B 2034/301* (2016.02)

(58) Field of Classification Search
CPC .............. A61B 17/22031; A61B 17/50; A61B 17/22012; A61B 2017/00017; A61B 2017/2215; A61B 17/221
See application file for complete search history.

(56) References Cited

U.S. PATENT DOCUMENTS

| | | |
|---|---|---|
| 7,879,070 B2 | 2/2011 | Ortiz et al. |
| 2005/0203382 A1 | 9/2005 | Govari et al. |
| 2007/0179525 A1 | 8/2007 | Frecker et al. |

(Continued)

OTHER PUBLICATIONS

Doby, T. Cerebral angiography and Egas Moniz. AJR Am J Roentgenol. Aug. 1992;159(2):364.

(Continued)

*Primary Examiner* — Thomas McEvoy
(74) *Attorney, Agent, or Firm* — Mintz Levin Cohn Ferris Glovsky and Popeo, P.C.

(57) ABSTRACT

The present disclosure relates to electrically controllable surgical tools. In general, surgical devices are provided having an electrically controllable, fingered operating end for use in angiography, endovascular and/or neurological surgery. The finger(s) at the operating end can be made from ionic polymer metal composite (IPMC) material to facilitate control of the finger(s).

14 Claims, 6 Drawing Sheets

(56) References Cited

U.S. PATENT DOCUMENTS

| | | | |
|---|---|---|---|
| 2008/0125706 A1 | 5/2008 | Sutermeister et al. | |
| 2010/0056953 A1 | 3/2010 | Couvillon, Jr. | |
| 2011/0202088 A1 | 8/2011 | Eckhouse et al. | |
| 2012/0169184 A1* | 7/2012 | Pelrine | H01L 41/0986 310/365 |
| 2014/0214004 A1 | 7/2014 | Millett | |
| 2015/0173673 A1* | 6/2015 | Toth | A61B 5/04001 600/301 |

OTHER PUBLICATIONS

Duarte et al., Editorial. Egas moniz, the pioneer of cerebral angiography. Interv Neuroradiol. Jun. 30, 1997;3(2):107-11.

Kim et al., Ionic Polymer-Metal Composites—II. Manufacturing Techniques. Smart Materials and Structures. 2003;12(1):65-79.

McDowell et al., Time is Brain: A Critical Analysis of the EXTEND-IA and ESCAPE Trials. World Neurosurg. Jun. 2015;83(6):949-51.

Menon et al., Initial experience with the Penumbra Stroke System for recanalization of large vessel occlusions in acute ischemic stroke. Neuroradiology. Apr. 2011;53(4):261-6.

Saver et al., Solitaire™ with the Intention for Thrombectomy as Primary Endovascular Treatment for Acute Ischemic Stroke (SWIFT PRIME) trial: protocol for a randomized, controlled, multicenter study comparing the Solitaire revascularization device with IV tPA with IV tPA alone in acute ischemic stroke. Int J Stroke. Apr. 2015;10(3):439-48.

Shahinpoor et al., Artificial Muscles: Applications of Advanced Polymeric Nanocomposites. 1st Edition. Taylor and Frnacis Publishers, London and New York (2007), p. 26.

Shahinpoor et al., Ionic Polymer-Metal Composites—I. Fundamentals. Smart Materials and Structures. 2001;10:819-33.

Shahinpoor et al., Ionic Polymer-Metal Composites—III. Modeling and Simulation as Biomimetric Sensors, Actuators, Transducers and Artificial Muscles. Smart Materials and Structures. 2004;13(4):1362-88.

Shahinpoor et al., Ionic Polymer-Metal Composites—IV. Industrial and Medical Applications. Smart Materials and Structures. 2005;14(1):197-214.

Zhang et al., The Penumbra System for the Treatment of Acute Ischemic Stroke: Report of Two Cases. Turk Neurosurg. 2016;26(2):306-8.

International Search Report for PCT Application No. PCT/US17/57285 dated Mar. 1, 2018 (4 pages).

* cited by examiner

ELECTRICALLY CONTROLLABLE SURGICAL TOOLS

CROSS REFERENCE TO RELATED APPLICATIONS

The present application claims priority to U.S. Provisional Patent Application No. 62/410,830 entitled "Devices, Systems, And Methods For Endovascular Surgery" filed Oct. 20, 2016, which is hereby incorporated by reference in its entirety.

FIELD

The present disclosure relates to electrically controllable surgical tools. More particularly, the present disclosure relates to surgical devices having electrically controllable, fingered operating end for use in surgery, such as angiography, endovascular surgery, and/or neurological surgery.

BACKGROUND

Minimally invasive surgery is a surgical approach that is well-suited for small-scale surgery such as angiography, endovascular surgery, and neurological surgery. Endovascular surgery may be used to treat problems affecting the blood vessels, such as an aneurysm (e.g., a swelling or ballooning of the blood vessel) or a thrombus (e.g., an in situ blot clot within the vasculature system), while neurological surgery may be used to treat problems associated with any portion of the nervous system (e.g., neurovascular disease). Both endovascular and neurological surgery may involve making a small incision to access the vascular system and introducing a surgical tool (e.g., an endovascular graft, angiography device, thrombectomy device, etc.) that may be inserted through the arteries in a catheter and positioned at an appropriate location for the surgical procedure.

The surgical tools are generally similar to those used in open surgical procedures except they include an extension (e.g., a tubular extension) between the end of the tool entering the surgical field (e.g., the operable end of the tool, instrument, or device) and the portion gripped by the surgeon. However, the limited motion available at the operable end of current devices creates significant limitations. For example, most instruments or devices are rigid and are limited to motions of six degrees of freedom of motion (e.g., x, y, z, pitch, roll, and yaw) or less about the incision point and in/out translation. Furthermore, the instruments can limit the surgeon's ability to accurately perceive the force/interaction between the instruments and tissues/organs. Additionally, the size of such surgical tools makes them difficult to use in small blood vessels.

Accordingly, there is a need in the art for improved devices, systems, and methods for angiography, endovascular surgery, and/or neurological surgery.

SUMMARY

Various electrically controllable surgical tools are provided.

In one aspect, a surgical tool is provided that in one embodiment includes a tubular member having an operating end including one or more fingers configured to deform in response to an electric field, and first and second electrodes configured to provide the electric field. The operating end is configured to be advanced into vasculature of a patient within which the first and second electrodes are configured to provide the electric field, thereby causing deformation of the one or more fingers within the vasculature.

The surgical tool can have any number of variations. For example, each of the one or more fingers can be made from ionic polymeric metal composite (IPMC) material. For another example, each of the one or more fingers can be configured to selectively deform by bending inward relative to a longitudinal axis of the tubular member and by bending outward relative to the longitudinal axis of the tubular member. For yet another example, the surgical tool can include a wire extending along the tubular member and configured to provide electrical energy to the wire. For still another example, each of the one or more fingers can be configured to generate a second electric field in response to the deformation. For another example, the one or more fingers can be elongate members configured to extend distally from an open end of the tubular member. For yet another example, the one or more fingers can be configured to deform by bending inward relative to a longitudinal axis of the tubular member to grab an object within the vasculature, and when so deformed, configured to be moved into a lumen of the tubular member. For another example, the one or more fingers can be configured to deform by bending outward relative to a longitudinal axis of the tubular member to abut a clot on a wall of the vasculature, and when so deformed, the operating end can be configured to move to scrape the clot off the wall with the one or more fingers. For yet another example, the one or more fingers can be configured to deform by vibrating, and the vibration of the one or more fingers can be effective to liquefy a clot within the vasculature. For still another example, the one or more fingers can be configured to sense at least one of arterial wall pressure, local hemodynamic blood pressure, and local blood flow velocity and direction. For another example, the surgical tool can include a control mechanism configured to be manually actuated by a user to cause the first and second electrodes to provide the electric field and thereby deform the one or more fingers. For still another example, the tubular member can be flexible.

In another embodiment, a surgical tool includes a tubular member having one or more electrically controllable elongate members attached thereto that are made from ionic polymeric metal composite (IPMC) material and are configured to move between an active mode and an inactive mode. The one or more electrically controllable elongate members are configured to move from the inactive mode to the active mode in response to introduction to an electric field. The one or more electrically controllable elongate members are configured to move from the active mode to the inactive mode in response to removal of the electric field. The tubular member is configured to be introduced into a body lumen of a patient and the one or more electrically controllable elongate members are configured to move from the inactive mode to the active mode within the body lumen.

The surgical tool can have any number of variations. For example, the one or more electrically controllable elongate members in the active mode can be configured to grab an object within the body lumen and to move relative to the tubular member to pull the object within an inner passageway of the tubular member. For another example, the one or more electrically controllable elongate members in the active mode can be configured to scrape a clot off a wall of the body lumen. For yet another example, the one or more electrically controllable elongate members can angularly adjust relative to a longitudinal axis of the tubular member when moving between the active and inactive modes.

In another aspect, a surgical method is provided that in one embodiment includes introducing an operating end of a surgical tool into vasculature of a patient. The surgical tool includes one or more electrically controllable fingers made from ionic polymeric metal composite (IPMC) material. The method also includes positioning the operating end at a desired position relative to a target object within the vasculature, and then exposing one or more electrically controllable fingers extending from the surgical tool to an electric field and thereby causing the one or more electrically controllable fingers to move relative to the target object and effect a desired action on the target object.

The surgical method can vary in any number of ways. For example, the desired action can include one of grasping the target object with the one or more electrically controllable fingers, scraping the target object off a wall of the vasculature with the one or more electrically controllable fingers, and liquefying the target object. For another example, the method can include actuating a manual control mechanism to deliver electrical energy to electrodes of the surgical tool and thereby create the electric field. For yet another example, the target object can be a clot.

In one aspect, an endovascular surgical tool is provided that in one embodiment includes an operating end including one or more distal dexterity units each having an actuation mode and a sensing mode; a housing operably coupled to the operating end; and a catheter operably coupled to the housing.

BRIEF DESCRIPTION OF DRAWINGS

For a fuller understanding of the nature and desired objects of the present disclosure, reference is made to the following detailed description taken in conjunction with the accompanying drawing figures wherein like reference characters denote corresponding parts throughout the several views and wherein.

DETAILED DESCRIPTION

Figure 1:
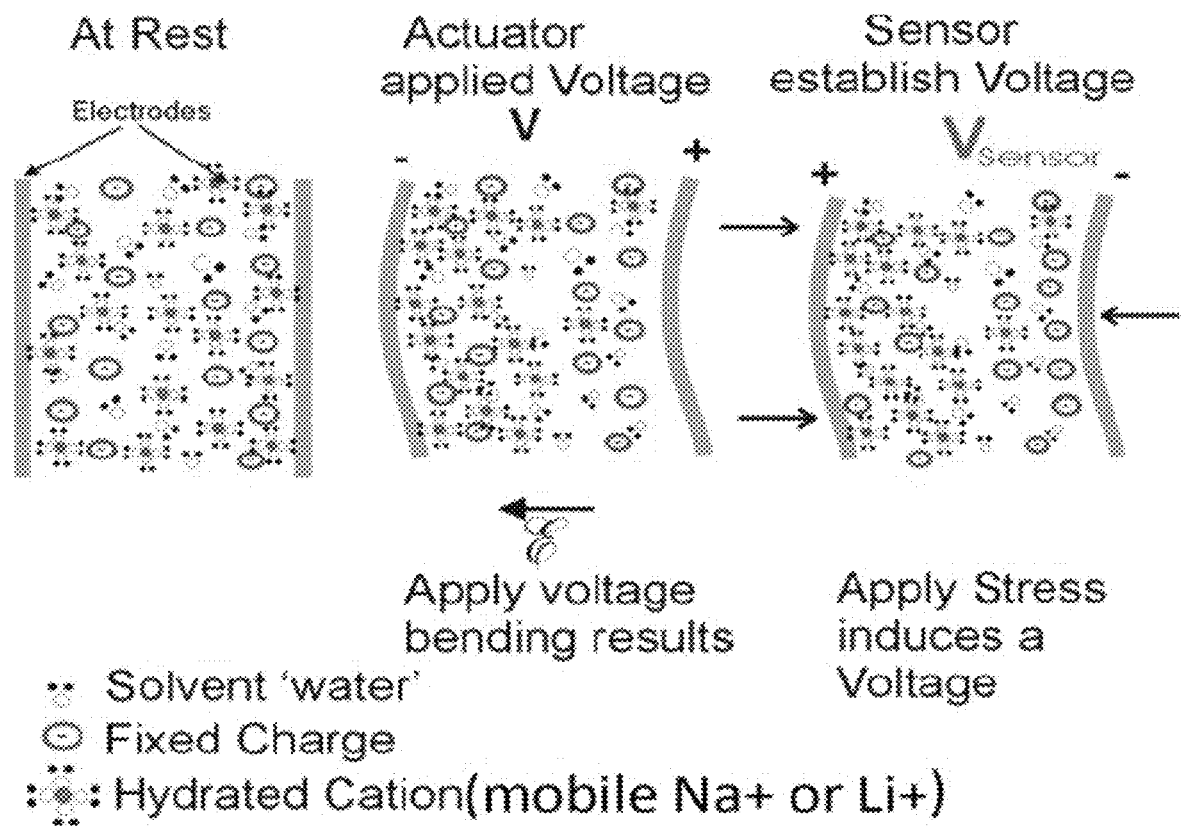
FIG. 1 depicts the basic mechanisms of actuation and sensing in ionic polymer metal composite (IPMC) actuators according to an exemplary embodiment of the disclosure.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

The present disclosure features devices, systems, and methods for use in the performance of surgical, diagnostic, or therapeutic methods and/or techniques relating to angiography, endovascular surgery, and/or neurological surgery. The present disclosure is based, at least in part, on the discovery that ionic polymer metal composite (IPMC) actuators and sensors may be combined with catheter/guidewire systems to produce electrically controllable and switchable surgical tools for a wide variety of surgical applications, such as endovascular surgical applications and neurological surgical applications. In particular, the present systems, apparatuses, and methods are suitable for performing minimally invasive techniques whereby the operable end of the surgical tool is capable of moving with degrees of freedom comparable to that seen when using open surgery techniques. Additionally, the present systems, apparatuses, and methods are particularly suitable for performing minimally invasive techniques/procedures under what might be considered challenging conditions for conventional minimally invasive techniques like operating within small, tortuous confines such as, for example, those presented by the vascular/neurovascular system. The devices, systems, and methods of the present disclosure may provide one or more benefits, such as any one or more of: (1) No radiation exposure to the treating physician and team, (2) Smarter tools that can drive to the treatment target without delay, sense any impending complication, and conform to whatever shape is necessary without multiple devices, (3) The potential to leverage the technology to battlefield or underserved regions of the world where such surgeries can be performed robotically from a long geographic distance, and (4) Accuracy so that the rate of complication from hemorrhage or vascular injury is minimized.

There currently exist no minimally invasive surgical systems that are both well-suited for endovascular and/or neurological surgery (e.g., angiography, thrombectomy, and the like) and electrically controllable/switchable. The few existing systems on the market are all mechanically controllable by the surgeon. Unfortunately, the control means for such mechanical systems are generally manual and hard to implement and may be unsafe.

Exemplary prior art mechanical devices are generally used to decrease the time taken for surgery (e.g., thrombus removal) and to possibly reduce the risk of prolonged infusion. For example, percutaneous mechanical angiography and thrombectomy (PMT) devices may be categorized as rotational, rheolytic, or ultrasound enhanced. Rotational devices such as the Trerotola device (Arrow International, PA, USA) and the Amplatz angiography and thrombectomy device (Microvena, MN, USA) employ a high velocity rotating helix to macerate a thrombus during a thrombectomy. The Trellis™ device (Covidien, Bacchus Vascular, CA, USA) employs an oscillating rather than rotating sinusoidal Nitinol wire between proximal and distal balloons while at the same time infusing thrombolytic agents in a segment 'isolated' by the balloon. The AngioJet® device (Possis, MN, USA) generates a high-pressure saline jet to create a pressure gradient resulting in rheolytic angiography and thrombectomy with aspiration of the softened thrombus into the catheter. Ultrasound assisted devices such as, for example, EKOS® Endowave™ device (EKOS Corporation, WA, USA), contain multiple ultrasound transducers that emit high frequency, low energy ultrasound energy in a radial fashion to enhance the penetration of thrombolysis by exposing plasminogen receptor sites. The Snare kit (Ev3, Inc., MN, USA) is constructed of Nitinol cable and a gold plated tungsten loop such that the pre-formed snare loop can be introduced through catheters without risk of snare deformation because of the snare's super-elastic construction. Similarly, the Alligator™ retrieval system (Ev3, Inc.) features a four pronged claw and is indicated for intra-cranial use. The MegaVac™ system by Capture Vascular, Inc. (CO, USA) provides occlusion, aspiration, and retraction of a clot but has the disadvantage of still being entirely mechanical and manually operated by the surgeon. Additionally, examples of retriever devices for acute stroke include the Solitaire™ device (Medtronic, MN, USA), the ERIC® stentriever device (MicroVention, CA, USA), and the Trevo® device (Stryker, MI, USA).

The few commercially available robotic tools for endovascular surgery are primitive in nature. For example, these tools function to drive catheters once in place, but are hand driven up until the step of stent delivery. Additionally, the tool driving the stent placement is itself external. Currently, there is no single robotic platform or set of robotic tools that can be used from vascular access to vascular closure.

The present disclosure provides an electrically controllable, soft, and biomimetic multi-fingered robotic grabber/retriever system at the distal tip of a guide wire and the enveloping micro catheter that enables a surgeon to electrically control, grab, retrieve, steer, stir and actively move the distal tip multi-fingered robotic fingers in a variety of surgical applications such as, for example, to manage clots, thrombi, platinum coils, stents, flow diverters, while allowing other occlusive objects to be captured and drained out of the vascular network. The system can also be employed in sensing wall pressure, local blood pressure, or local blood flow velocity and hemodynamics. Advantageously, the present disclosure may be configured as a robotic platform.

The human vasculature (arteries and veins) is an ideal system in which to develop a robotic platform and tools for angiography and endovascular surgery. Once access is gained to the vasculature, any organ system may be reached despite anatomic variation. For example, even the access to the arterial or venous systems may be guided with imaging technology, ultrasonic technology, or electromechanical sensors. The navigation may be done both externally through the injection of contrast medium while x-ray imaging is concurrently performed, or internally via angioscopic techniques. The surgical targets of disclosure are generally geometrically defined targets such as, for example, a cerebral aneurysm, blocked artery, and the like. In an exemplary embodiment, the present disclosure may be well-suited for applications such as thrombectomy and angiogenesis.

Thrombectomy

In randomized trials, the current generation of stent retrievers for thromboembolism in the brain have just over 80% chance of success in clot retrieval when combined with tissue plasminogen activator (tPA). For example, see Saver J L, Goyal M, Bonafe A, et al., "Solitaire with the Intention for Angiography and thrombectomy as Primary Endovascular Treatment for Acute Ischemic Stroke (SWIFT PRIME) trial: protocol for a randomized, controlled, multicenter study comparing the Solitaire revascularization device with IV tPA with IV tPA alone in acute ischemic stroke," International journal of stroke: official journal of the International Stroke Society 2015; 10:439-48; and McDowell M M, Ducruet A F, "Time Is Brain: A Critical Analysis of the EXTEND-IA and ESCAPE Trials," World neurosurgery 2015; 83:949-51. For longer clots over 8 mm, that number drops to just over 70%. Devices that are soft, tubular non-retrievable stents are typically placed into the clot, allowed to sit for a few minutes, ideally intercalating the clot, and then pulled out under flow reversal or occlusion. The figures for successful retrieval, although substantially improved over the previous generations, continue to be sub-optimal. Reasons for failure to retrieve a clot can relate to clot composition, clot level, and proximal anatomical tortuosity. Very calcified emboli, and very soft clots pose difficulties for stent retrievers to engage and then retain the clot with removal. Both proximal and distal tortuosity can make access challenging because not enough stability is established to engage and pull the clot out. There is a separate set of angiography and thrombectomy tools that are suction catheters used alone or in conjunction with retrievers, but these have not been vetted in randomized trials. For example, see Menon B K, Hill M D, Eesa M, et al., "Initial experience with the Penumbra Stroke System for recanalization of large vessel occlusions in acute ischemic stroke," Neuroradiology 2011; 53:261-6; and Zhang X, Gao J W, Jabbour P., "The Penumbra System for the Treatment of Acute Ischemic Stroke: Report of Two Cases," Turkish neurosurgery 2016, 26:306-8. Without being bound by theory, it is believed that these systems may be disadvantageous because thromboembolism creates, to some degree, a collapsed vessel that suction alone could theoretically worsen, which would make suction a poor standalone strategy.

Angiography

Cerebral angiography was invented by Egas Moniz, a Portuguese neurologist, in 1927. For example, see Duarte G, Goulao A., Editorial, "Egos moniz, the pioneer of cerebral angiography." Interventional Neuroradiology: Journal Of Peritherapeutic Neuroradiology, Surgical Procedures And Related Neurosciences, 1997, 3:107-11; and Doby T., "Cerebral angiography and Egas Moniz," AJR American Journal Of Roentgenology 1992, 159:364. Since 1927, the technique has been refined and made safer, with the risk of cerebral angiography being less than one-third of one percent for any unexpected complication. Even with the development of advanced non-invasive imaging techniques, cerebral angiography remains one of the key tools to image the blood vessels of the brain for diagnosis of neurological disease and for neurosurgical planning. The technique has become even more important with the progressive development of the tools and techniques of endovascular neurosurgery (interventional neuroradiology, neurointervention). This growing field treats acute ischemic stroke, vertebral and carotid vascular stenosis and occlusion, cerebral aneurysms, cerebral arteriovenous malformations, and cerebral fistulas through minimally invasive techniques using femoral, radial, or brachial artery access. The access tools and imaging techniques for these minimally invasive treatments have cerebral angiography as their foundation. Over the last two decades there have been tremendous advances in computerized tomography and magnetic resonance imaging techniques that can image the blood vessels of the head and neck in three dimensions. However, these non-invasive techniques have not replaced angiography for three major reasons. First, for lesions (e.g., aneurysms) smaller than 5 mm they remain spatially poor at characterizing the anatomical relationships. Furthermore, formal angiography, especially three-dimensional (3D) cerebral angiography, allows for nearly an infinite range of angles with which to study intracranial vascular pathology. Second, the ability of angiography to look at the pattern of leptomeningeal flow and to assess direct and collateral circulation is critical to diagnosis and surgical planning. Third, access from the point of sheath entry to the lesion is critical to understand and to know how to treat and the safety of treatment of any vascular lesion in the brain and this is best assessed with angiography.

In view of the foregoing, the present disclosure provides, in general, a tool for vascular/neurological surgery that has enhanced surgical capabilities, high reliability and safety, and remote operability, which also eliminates or minimizes radiation exposure to staff.

According to the techniques herein, the present disclosure integrates ionic polymer metal composite (IPMC) actuators and sensors with catheter/guidewire systems to produce electrically controllable and switchable surgical tools for a wide variety of surgical applications, such as endovascular and neurological surgical applications. The integration of soft IPMC actuators and sensors with catheter/guidewire systems may confer advantages onto the devices, systems, and methods of the present disclosure, such as any one or more of: (1) the present devices, systems, and methods may provide a smart tool that can grab or wrap around a clot ideally improving capture rates; (2) the present devices, systems, and methods provide the first application of robotic surgical tools for intracranial endovascular neurosurgery and may have numerous applications for endovascular surgery throughout the whole body; (3) the present devices, systems, and methods may provide a complete robotic angiography platform including a soft biomimetic multi-fingered robotic configured to function as a combined retriever/angiography/thrombectomy system; (4) the present devices, systems, and methods may provide strong steering capability to allow surgeons to home in on cerebral aneurysms; (5) the present devices, systems, and methods may provide stirring (vibratory) distal end dynamics to break up blood clots, by liquefying them; and (6) the present devices, systems, and methods may provide stirring (vibratory) distal end dynamics to sense the arterial wall pressure or blood flow local velocities and direction of flow.

Ionic Polymer Metal Composites (IPMCs)

Figure 9:
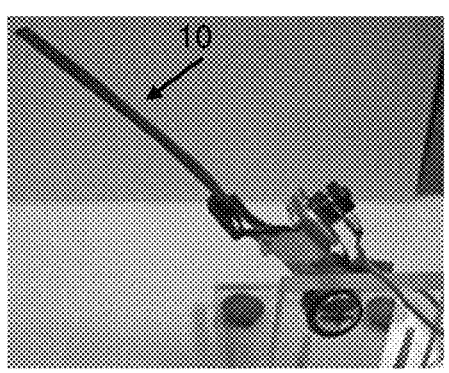
FIG. 9 depicts a non-deformed IPMC strip according to an exemplary embodiment of the disclosure.
Figure 10:
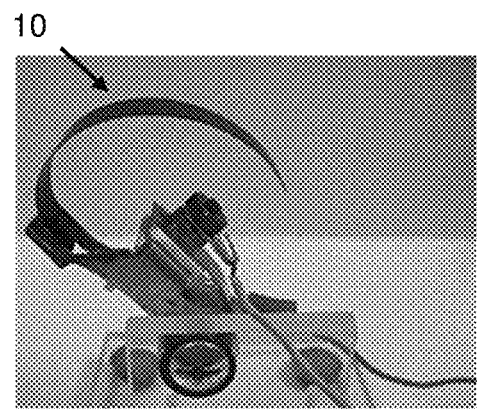
FIG. 10 depicts the IPMC strip of FIG. 9 in a deformed state according to an exemplary embodiment of the disclosure.

IPMCs belong to a family of electroactive polymers that deform spectacularly (actuation mode) in a small imposed electric field (e.g., in a range of 10 to 15 V/mm). For example, FIG. 9 shows one embodiment of an IPMC strip or finger 10 in a relaxed or non-deformed state, and FIG. 10 shows the IPMC strip 10 in a deformed state in a small imposed electric field under a step voltage of about 4 V, with current of about 150 mA.

Additionally, IPMCs also generate electrical fields (e.g., in a range of 1 to 5 millivolts in sensing and energy harvesting mode) in response to physical deformation imparted upon them mechanically or by environmental dynamics, such as wind or ocean waves, and in endovascular surgery by factors such as blood flow velocities or dynamics. IPMCs function both in air and in or under liquids such as water or blood. Advantageously, IPMCs may be encapsulated in thin elastic encapsulates (e.g., Silicone, Saran or polyvinylidene chloride (PVDC), and dimethyl sulfoxides (DMSOs)) to keep their moisture content constant, which allows for uniform and consistent operation. For example, see Shahinpoor, M. and K. J. Kim, "Ionic Polymer-Metal Composites—I. Fundamentals," (Review Paper), Smart Materials and Structures Int. J., Vol. 10, pp. 819-833 (2001); Kim, K. J. and M. Shahinpoor, "Ionic Polymer-Metal Composites—II. Manufacturing Techniques", Smart Materials and Structures (SMS) Int. J., Institute of Physics Publication, Vol. 12, No. 1, pp. 65-79, (2003); Shahinpoor, M. and K. J. Kim, "Ionic Polymer-Metal Composites—III. Modeling and Simulation as Biomimetic Sensors, Actuators, Transducers and Artificial Muscles" (Review Paper), Smart Materials and Structures Int. J., vol. 13, No. 4, pp. 1362-1388, (2004); Shahinpoor, M. and K. J. Kim, "Ionic Polymer-Metal Composites—IV. Industrial and Medical Applications" (Review Paper), Smart Materials and Structures Int. J., Vol. 14, No. 1, pp. 197-214, (2005); and Shahinpoor, M., Kim K. J. and M., Mojarrad, "Artificial Muscles: Applications of Advanced Polymeric Nano-Composites, First Edition, Taylor and Francis Publishers, London and New York, (2007).

IPMCs are synthetic nanocomposites that display artificial muscle-like behavior under an applied electric field. IPMCs may be composed of an ionic polymer such as, for example. Nafion™ or Flemion™, with boundary surfaces chemically plated or physically coated with conductors such as platinum, gold, palladium, silver, aluminum, graphite, graphene, conductive polymers or synthetic metals. One skilled in the art will appreciate that any appropriate conductive metal may be used for this application. Under an applied voltage (e.g., in a range of about 1 to 4 V for typical 10 mm×40 mm×0.2 mm samples or an electric field in a range of about 1 to 5 V/mm), ion migration and redistribution due to the imposed voltage across a strip of IPMCs results in bending and twisting deformations. If the electrodes are placed on the surfaces of the IPMC sample in a nonsymmetric configuration, the imposed voltage can induce a variety of deformations such as twisting (torsion), rolling, turning, twirling, and non-symmetric bending. Alternatively, if such deformations are physically applied to IPMC strips they generate an output voltage signal (a few millivolts for typical small samples of 1 cm×4 cm×0.3 mm) and may function as sensors and/or energy harvesters. IPMCs have a force density of about 40 in a cantilever configuration. In other words, they can generate a tip force of almost 40 times their own weight in a cantilever configuration. For example, see Shahinpoor, M., Kim K. J. and M., Mojarrad, "Artificial Muscles: Applications of Advanced Polymeric Nano-Composites," First Edition, Taylor and Francis Publishers, London and New York, (2007). IPMCs in actuation, sensing and energy harvesting modes have a very broad bandwidth that may span from a fraction of a hertz to mega HZ and higher. IPMCs were first introduced in 1998 by Shahinpoor, Bar-Cohen, Xue, Simpson and Smith. For example, see Shahinpoor, M. and K. J. Kim, "Ionic Polymer-Metal Composites—I. Fundamentals" (Review Paper), Smart Materials and Structures Int. J., Vol. 10, pp. 819-833 (2001); and Kim, K. J. and M. Shahinpoor, "Ionic Polymer-Metal Composites—II. Manufacturing Techniques," Smart Materials and Structures (SMS) Int. J., Institute of Physics Publication, Vol. 12, No. 1, pp. 65-79, (2003). The essential mechanism for both actuation and sensing/energy harvesting capabilities of IPMCs is the transport of cations (typically Na+, Li+) towards the cathode electrode and away from the anode electrode due to either an imposed electric field (actuation) or an imposed deformation field or osmotic pressure gradient (sensing/energy harvesting).

FIG. 1 graphically displays the actuation and sensing mechanisms in bending strips of IPMCs. Ionic polymer metal composites (IPMCs) are active multi-functional smart materials, i.e., they deform significantly when excited by a relatively low voltage and generate voltage when deformed. For example, the essential mechanism involved during actuation is based on cation migration from the anode side to the cathode side under the influence of an imposed electric field across the finger/muscle (e.g., IPMC). As this happens, the cations that have migrated to the cathode side expand the cathode side of the finger/muscle and causes the finger/muscle to bend towards the anode side. While in the sensing mode, the mechanical deformation or bending of the fingers/muscles due to external means may cause the cations to re-distribute or be forced to migrate and thus produce electricity based on Maxwell-Poisson-Nernst-Planck equations. For example, see Kim, K. J. and M. Shahinpoor, "Ionic Polymer-Metal Composites—II. Manufacturing Techniques," Smart Materials and Structures (SMS) Int. J., Institute of Physics Publication, Vol. 12, No. 1, pp. 65-79, (2003).

Figure 2:
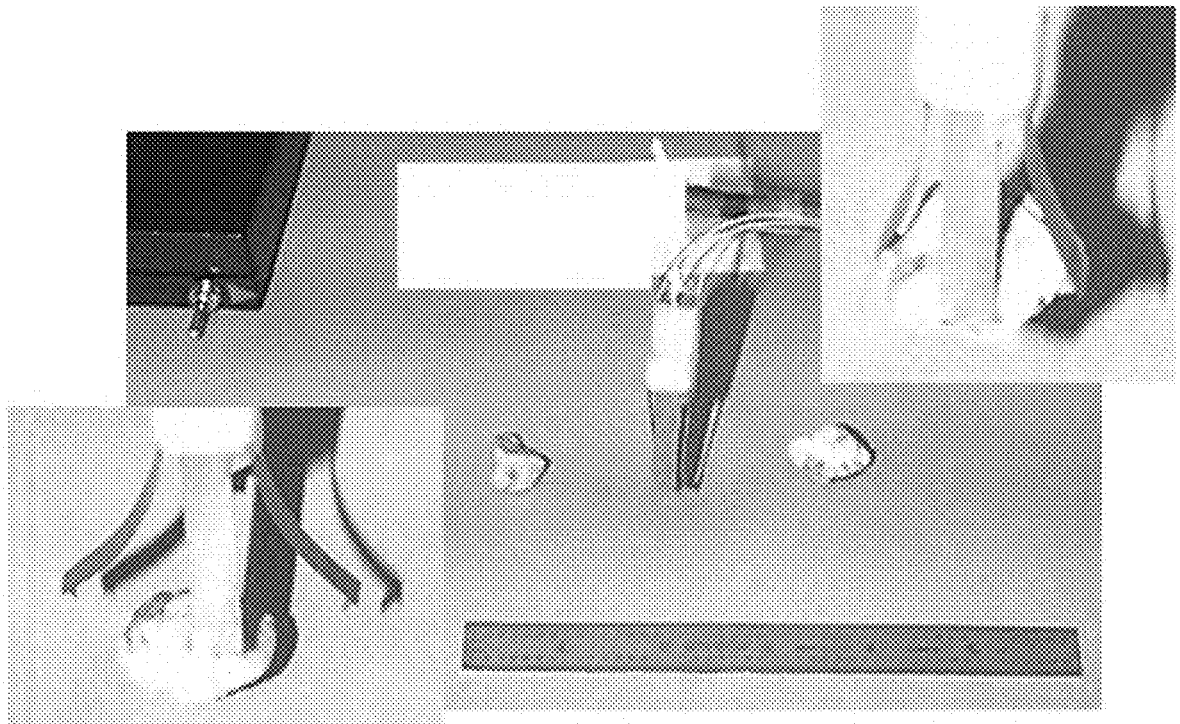
FIG. 2 depicts an electrically controllable occlusion retriever in, open, and closed positions according to an exemplary embodiment of the disclosure.

FIG. 2 displays typical deformation of a strip of IPMC under a low voltage. In the illustrative example, IPMC bending is toward the anode electrode and is proportional to the applied voltage (e.g., as voltage increases the bending increases). If the voltage is dynamic, e.g. sinusoidal, the bending becomes oscillatory. IPMCs have a very large bandwidth from a fraction of a hertz to about 0.5 megahertz both in actuation and sensing. Once an electric field is imposed on an IPMC cantilever, the conjugated and hydrated cations rearrange to accommodate the local electric field and thus the network deforms or bends in a spectacular manner under a small electric field such as 10's of volts per millimeter; however, one skilled in the art will appreciate that the size of the electric field may vary with the size of the IPMC finger/muscle. As shown in FIG. 2, this deformation may be put to mechanical advantage in the form of a grabbing movement. It is contemplated within the scope of the invention that these IPMC fingers/muscles may respond to the type and dynamics of an imposed voltage. For example, if the imposed voltage is sinusoidal then the IPMC may also vibrate sinusoidally, while if the voltage or applied field is asymmetric, then the deformation may also be asymmetric and undulating.

IPMCs are excellent for sensing stress, arterial wall pressure, local blood pressure, strain, blood flow velocities, and complex deformations and vascular kinesthetics of the environment in which they are sensing and simultaneously actuating.

Figure 3:
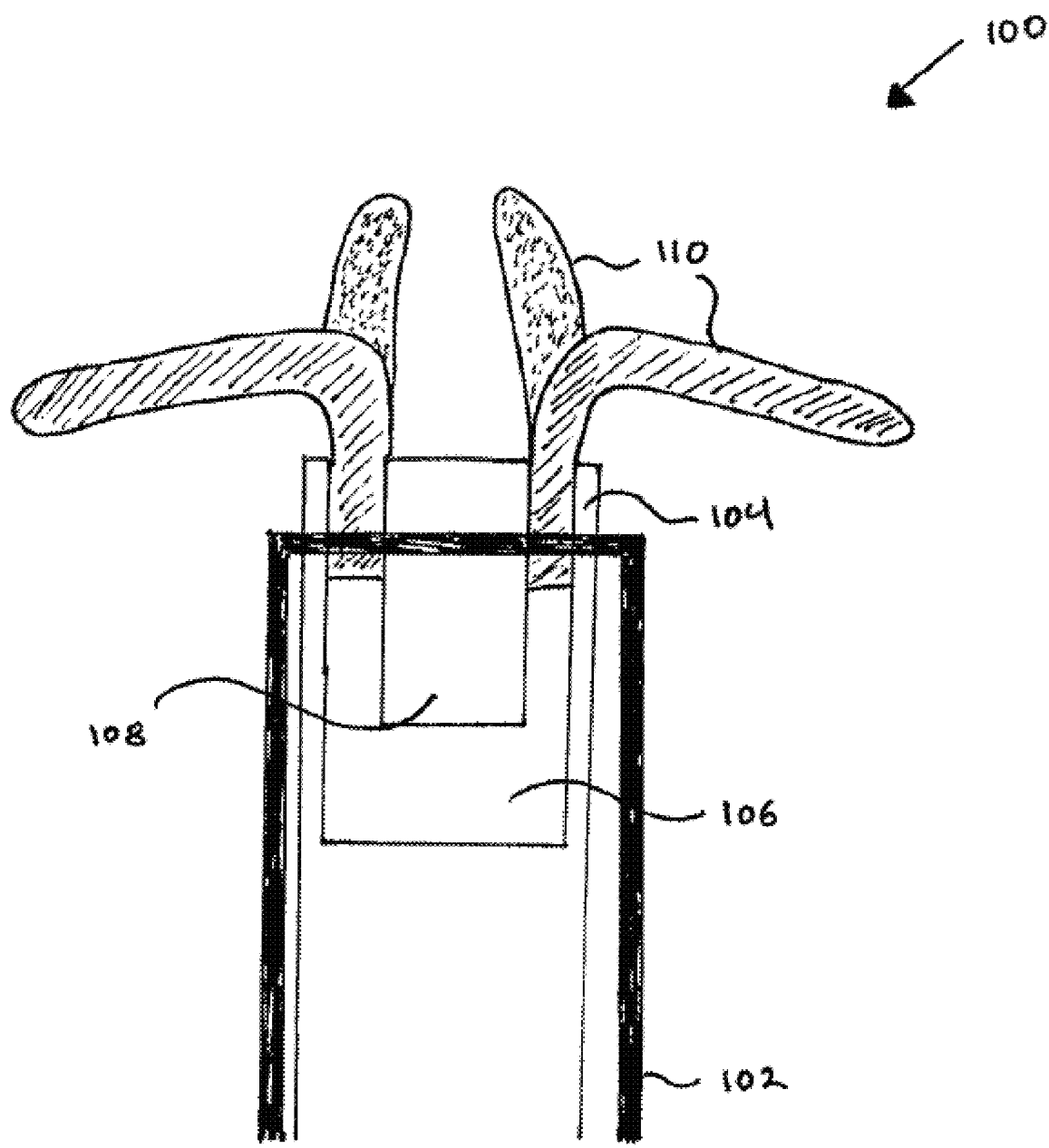
FIG. 3 depicts an electrically controllable and switchable surgical tool according to an exemplary embodiment of the disclosure.

FIG. 3 depicts an illustrative embodiment of an electrically controllable and switchable surgical tool for a wide variety of endovascular/neurological surgical applications according to the present disclosure. In particular, operating end 100 may include a catheter 102 configured to hold housing 104, which may be configured to house one or more distal appendages 110. The surgical tool in this illustrative embodiment has two distal appendages 110. In the illustrative embodiment shown, two distal appendages 110 are shown in the open position (slash shading) or the closed position (dotted shading). In an illustrative embodiment, operating end 100 may have one, two, three, or four distal appendages 110, although more distal appendages are possible. It is contemplated within the scope of the disclosure that housing 104 may be any of a variety of suitable housings such as, for example, a guidewire, a metal housing, a plastic housing, a ceramic housing, and the like. Housing 104 may be configured to include external electrode 106 and internal electrode 108, as in this illustrative embodiment. In an exemplary embodiment, external electrode 106 has a u-shaped cross sectional aspect with a distal surface configured to abut and/or adjoin and/or receive a proximal end of the one or more distal appendages 110. The one or more distal appendages 110 in this illustrative embodiment are made of one or more IPMCs, as described above, and are operatively connected to external electrode 106 and internal electrode 108 in a number of ways such as, for example, soldering, bonding, gluing, welding, friction fitting, force fitting, pressure fitting, and the like.

Figure 4:
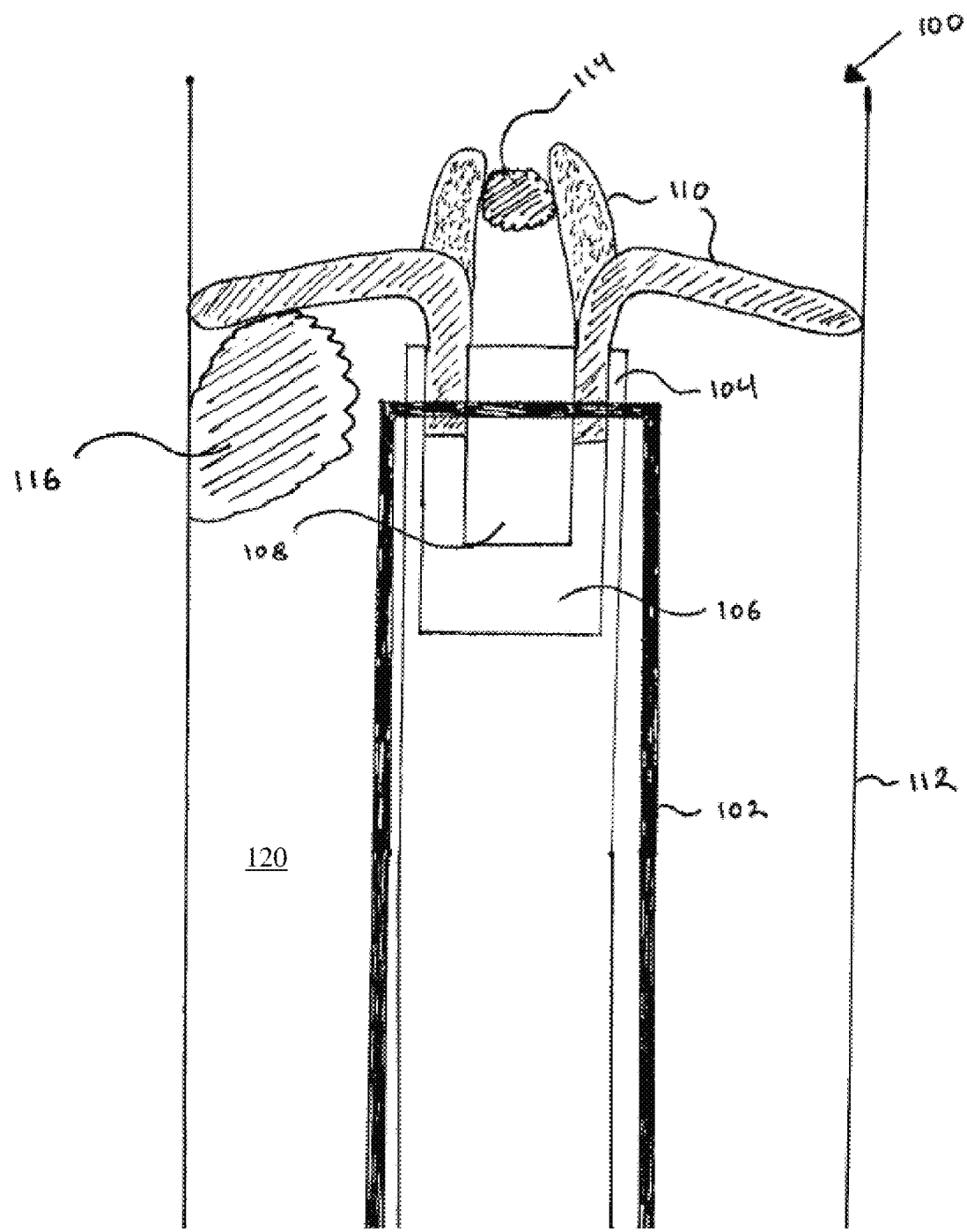
FIG. 4 depicts the electrically controllable and switchable surgical tool of FIG. 3 removing clots within the vasculature system according to an exemplary embodiment of the disclosure.

FIG. 4 depicts an illustrative embodiment of the electrically controllable and switchable surgical tool of FIG. 3 according to the present disclosure in the process of removing exemplary blood clots 114 and 116. Other embodiments of electrically controllable and switchable surgical tools as described herein can be similarly used. As shown in FIG. 4, operating end 100 may be appropriately positioned between the walls 112 and in the lumen 120 of an artery or vein at a desired position at which the operating end 100 is configured to remove clot 114 by a "grabbing" mechanism, clot 116 by a "scraping" mechanism, or either clot 114, 116 by a "stirring" mechanism to liquefy the clot, depending upon how electric control signals are applied to the distal appendages 110. One skilled in the art will appreciate that the ability to deform the one or more distal appendages 110 in any of a variety of configurations may allow operating end 100 to serve a variety of functions such as, for example, grabbing, scraping, liquefying, disrupting or breaking, prying, retrieving, cleaning, etc.

For example, it is contemplated within the scope of the invention that operating end 100 may be used as a retriever of lost objects within the vascular system. In one embodiment of object retrieval using the surgical tool of FIG. 3 or other surgical tool embodiments described herein, the proposed retriever may be employed by neurovascular surgeons in the form of an electrically controllable and switchable endovascular active tubular catheter/guidewire equipped with one or more multi-fingered soft dynamic appendages, e.g., the appendages 110, made with ionic polymer metal composite (IPMC) actuators, sensors, and artificial muscles. The active tubular guidewire housed in the lumen of a micro catheter may allow a vascular or neuro surgeon to reach the interior portions of a patient's vasculature. In one illustrative embodiment, operating end 100 may include a multi-fingered robotic gripping portion having multiple dynamically electrically bendable soft fingers made with platinum-plated soft IPMC fingers deformable to grab or release any object within the vasculature and retrieve it by means of electrical activation of the polymeric muscles (IPMCs) by a low voltage in a range of about 1 to −1.4 volts. The surgeon may continuously observe the retriever fingers fluoroscopically due to presence of MRI-compatible platinum electrodes on the IPMC soft fingers.

Figure 5:
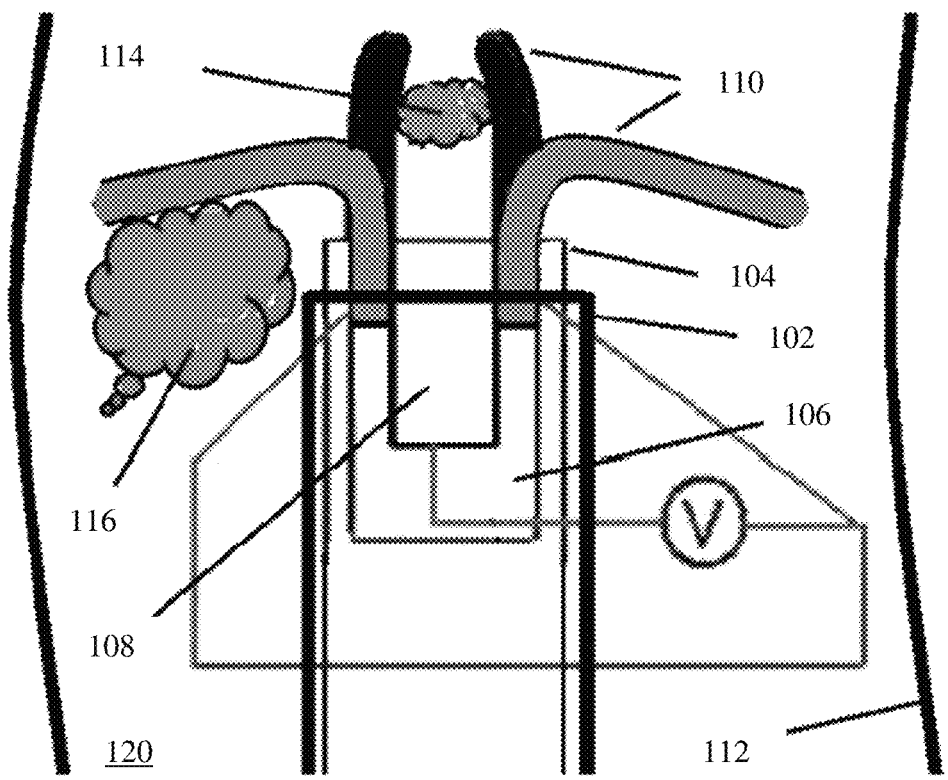
FIG. 5 depicts control of the electrically controllable and switchable surgical tool of FIG. 4 removing clots within the vasculature system according to an exemplary embodiment of the disclosure.

Referring again to the clot removal of FIG. 4, as shown in FIG. 5, operating end 100 may be electrically controllable by application of an electric current to external electrode 106 and/or internal electrode 108.

Figure 6:
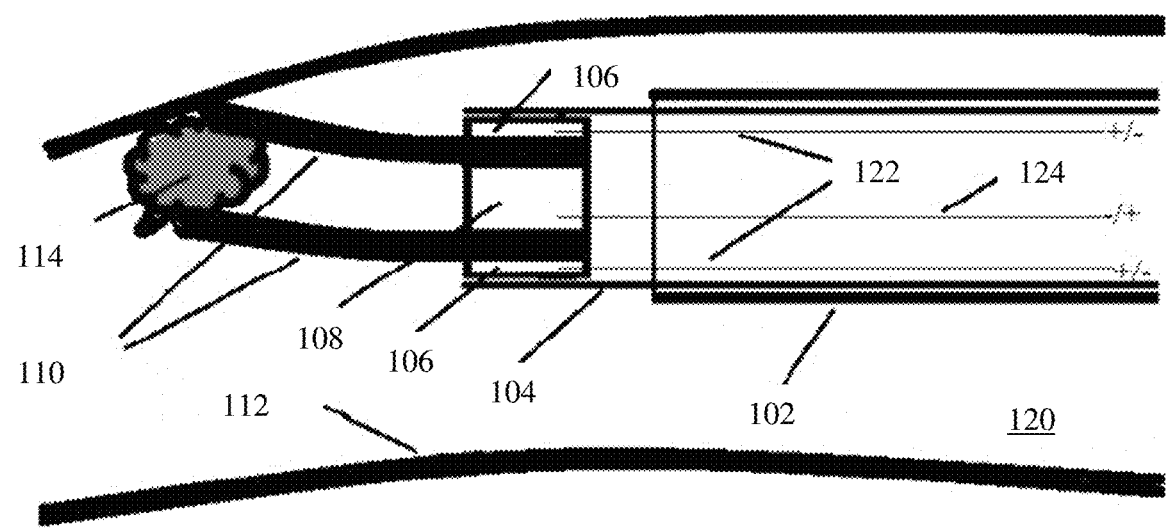
FIG. 6 depicts exemplary wiring for the electrically controllable and switchable surgical tool of FIG. 4 removing clots within the vasculature system according to an exemplary embodiment of the disclosure.
Figure 8:
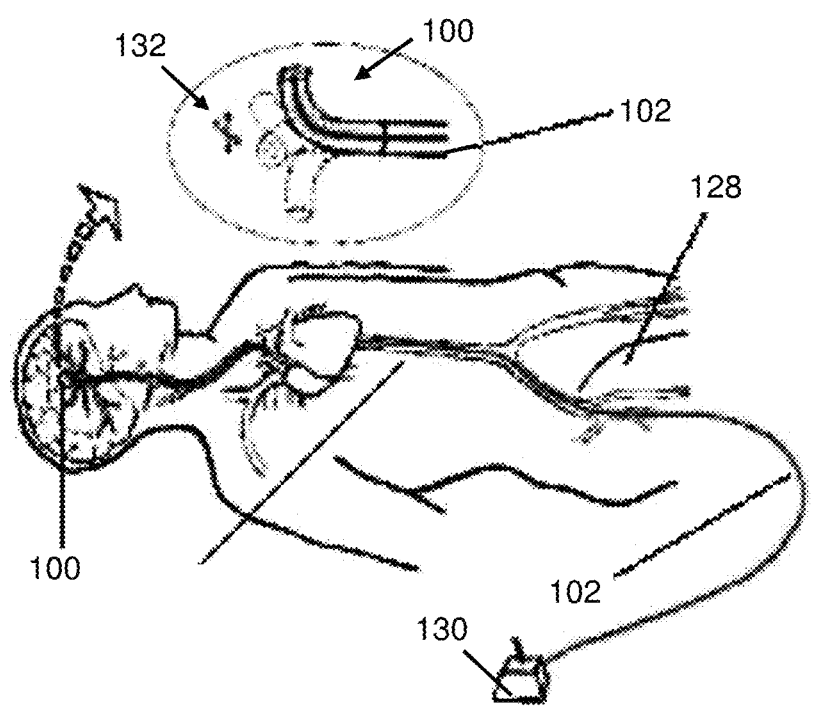
FIG. 8 depicts the electrically controllable and switchable surgical tool of FIG. 4 in a neurological context according to an exemplary embodiment of the disclosure.

The electric current can be applied to the electrodes 106, 108 in a variety of ways. In this illustrative embodiment, as shown in FIG. 6, thin lead wires 122, 124 run through the cannula of the microcatheter 102 to reach the endovascular tip of the active housing/guide wire 104 equipped with the IPMC fingers 110. The wires 122, 124 are omitted from FIGS. 3-5 for clarity of illustration. In an illustrative embodiment, the voltage lead wires may be thin gold wires thorough the catheter or cannula carrying the low voltage to the distal tip of the retriever to actuate the IPMC fingers. As in this illustrative embodiment, one wire 124 may be bonded or attached to the internal electrode 108 and the other lead wire 122 may be attached to external electrode 106. A manual control mechanism, e.g., joysticks, foot pedals, and the like, may be used by the surgeon to dynamically deform and configure the multi-fingered operating end 100 of the IPMC retrieval system to capture any thrombus, embolus, coil, stent, flow diverter, lost objects or to actively dislodge any tightly adhered thrombus from the vasculature walls. Advantageously, the multi-fingered operating end 100 is easily activated and deactivated by surgeon via the manual control mechanism, such as by pushing a button, moving a joystick knob, or turning a switch on and off. FIG. 8, which is discussed further below, illustrates one embodiment of a manual control mechanism, in the form of a joystick 130, operatively connected to the wires 122, 124.

The fingers/muscles or appendages of an electrically controllable and switchable surgical tool may in various exemplary embodiments be made with biocompatible ionic Teflon in a nanocomposite form with MRI compatible and fluoroscopically opaque platinum (Pt). The active tubular guidewire housed in the lumen of a micro catheter may allow a vascular or neuro surgeon to reach the interior portions of a patient's vasculature or cerebra vasculature employing robotic angiography and thrombectomy. The devices, systems, and methods herein may include a multi-fingered robotic gripping portion having a multiple of dynamically electrically bendable soft fingers made with platinum-plated soft IPMC fingers deformable to grab or release any object within the vasculature and retrieve it by means of electrical activation of the polymeric muscles (IPMCs) by a low voltage of less than 1 volt. The surgeon may continuously observe the retriever fingers fluoroscopically due to presence of MRI-compatible platinum electrodes on IPMC soft fingers. A manual control mechanism, e.g., joysticks, foot pedals, and the like may be used by the surgeon to dynamically deform and configure the multi-fingered IPMC retrieval system to capture any thrombus, embolus, coil and stent, flow diverter, or lost objects or to actively dislodge any tightly adhered thrombus from the vasculature walls. The active endovascular multi-fingered IPMC object grabber may be easily activated and deactivated by surgeon pushing a button or turning a switch on and off.

Figure 7:
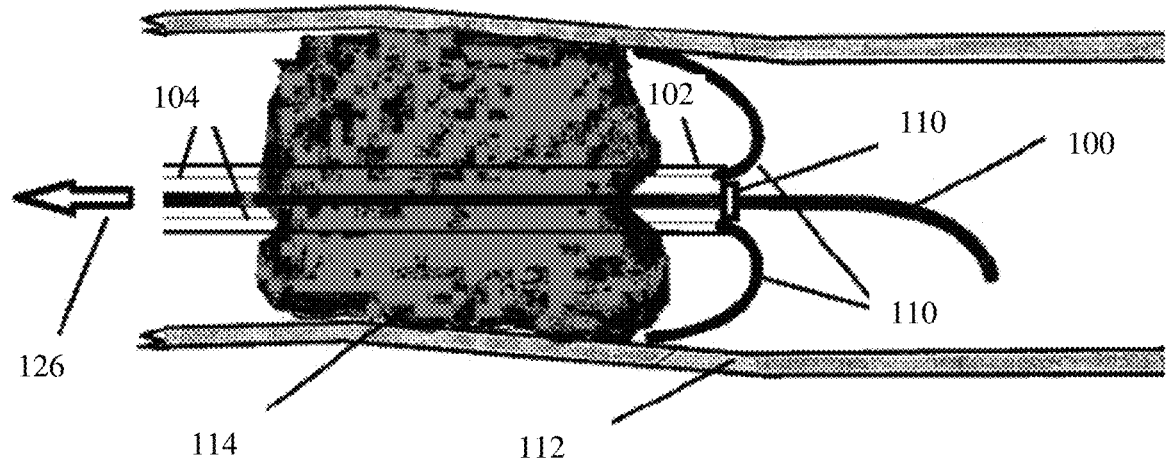
FIG. 7 depicts the electrically controllable and switchable surgical tool of FIG. 4 removing clots within the vasculature system according to an exemplary embodiment of the disclosure.

FIG. 7 depicts an illustrative embodiment of the electrically controllable and switchable surgical tool of FIG. 4 in the process of removing exemplary blood clot 114 via a mechanism in which the operating end 100 is pushed through the clot 114, the distal fingers 110 are actuated into a bent position, and then the catheter/guidewire/operating end assembly is pulled backwards in a backward or proximal direction shown by arrow 126, thereby removing the clot.

The artery or vein in which the operating end 100 of the surgical tool is positioned can be at a variety of locations within the patient, as discussed herein. For example, as shown in FIG. 8 using the surgical tool of FIG. 3 by way of illustrative example, the surgical tool can be used in a neurological context with the artery or vein being located in a brain of a patient 128, with the catheter 102 advanced into the patient's body such that the operating end 100 is located at a desired position within the brain. The inset of FIG. 8 depicts the operating end 100 adjacent a clots 132 and depicts example electrically controllable and switchable movement of the operating end 100 by dotted line drawing.

Specific benchmark modeling and experiments may be used to retrieve a lost platinum coil used in embolizing cerebral aneurysms by utilizing a standard benchmarking procedure for surgeons to compare in vitro the fabricated robotic retriever system with standard medical retrieving of lost objects within the human body vasculature. Extension of the capabilities of the above novel robotic angiography and thrombectomy system to also retrieve clot, thrombus, platinum coils, stents, flow diverters and other occlusive objects from the lumens in the human body vasculature, employing advanced robotic angiography and thrombectomy. Specifically, benchmarking will be implemented to capture, grab and retrieve a blood clot adhered to the inner walls of a vasculature and comparing the results with standard medical retrieving of lost objects within the human body vasculature. Dynamic modeling and numerical simulations of the novel soft biomimetic robotic angiography and thrombectomy system in terms of its dynamics within the vasculature and characterization and measurements of the mobilized retrieval force capabilities in connection with vascular safety and protection considerations.

As used in the specification and claims, the singular form "a," "an," and "the" include plural references unless the context clearly dictates otherwise.

Unless specifically stated or obvious from context, as used herein, the term "about" is understood as within a range of normal tolerance in the art, for example within 2 standard deviations of the mean. "About" may be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

As used herein, a "patient" is a vertebrate, preferably a mammal, more preferably a human. Mammals include, but are not limited to, murines, simians, humans, farm animals, sport animals, and pets.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

A person skilled in the art will appreciate that the implementations described herein have application in conventional minimally-invasive and open surgical instrumentation as well application in robotic-assisted surgery.

Although a preferred embodiment of the invention has been described using specific terms, such description is for illustrative purposes only, and it is to be understood that changes and variations may be made without departing from the spirit or scope of the following claims.

All patents, published patent applications and other references disclosed herein are hereby expressly incorporated by reference in their entireties by reference.

Those skilled in the art will recognize, or be able to ascertain using no more than routine experimentation, many equivalents of the specific embodiments of the invention described herein. Such equivalents are intended to be encompassed by the following claims.

One skilled in the art will appreciate further features and advantages of the invention based on the above-described embodiments. Accordingly, the invention is not to be limited by what has been particularly shown and described, except as indicated by the appended claims.

What is claimed is:

1. A surgical tool, comprising:
   a tubular member having an operating end including a plurality of fingers each configured to deform in response to a single electric field; and
   first and second electrodes configured to provide the electric field;
   wherein the operating end is configured to be advanced into vasculature of a patient within which the first and second electrodes are configured to provide the electric field, thereby causing deformation of the fingers within the vasculature; and
   wherein the first electrode is external to the second electrode, which is internal to the first electrode;
   wherein the fingers each extend distally from the first and second electrodes;
   wherein a distal surface of the first electrode is attached to a proximal surface of each of the fingers; and
   wherein the first electrode is U-shaped, and the distal surface of the first electrode includes distal surfaces at opposed terminal ends of the first electrode.

2. The tool of claim 1, wherein each of the fingers is made from ionic polymeric metal composite (IPMC) material.

3. The tool of claim 1, wherein each of the fingers is configured to selectively deform by bending inward relative to a longitudinal axis of the tubular member and by bending outward relative to the longitudinal axis of the tubular member.

4. The tool of claim 1, further comprising a wire extending along the tubular member and configured to provide electrical energy to the first and second electrodes.

5. The tool of claim 4, wherein the wire is configured to deliver a voltage to the first and second electrodes that induces the electric field.

6. The tool of claim 1, wherein each of the fingers is configured to generate a second electric field in response to the deformation.

7. The tool of claim 1, wherein the fingers are each an elongate member configured to extend distally from an open end of the tubular member.

8. The tool of claim 1, wherein the fingers are each configured to deform by bending inward relative to a longitudinal axis of the tubular member to grab an object within the vasculature, and when so deformed, configured to be moved into a lumen of the tubular member.

9. The tool of claim 1, wherein the fingers are configured to simultaneously deform by each bending outward relative to a longitudinal axis of the tubular member, and when so deformed, the operating end is configured to move to scrape a clot off a wall of the vasculature.

10. The tool of claim 1, wherein the fingers are each configured to deform by vibrating, the vibration being effective to liquefy a clot within the vasculature.

11. The tool of claim 1, wherein the fingers are each configured to sense at least one of arterial wall pressure, local hemodynamic blood pressure, and local blood flow velocity and direction.

12. The tool of claim 1, further comprising a control mechanism configured to be manually actuated by a user to cause the first and second electrodes to provide the electric field and thereby deform the fingers.

13. The tool of claim 1, wherein the tubular member is flexible.

14. The tool of claim 1, further comprising a housing that houses the fingers and the first and second electrodes and that is located within an inner lumen of the tubular member.

* * * * *